(12) United States Patent
Watkins, Jr. et al.

(10) Patent No.: US 7,414,416 B2
(45) Date of Patent: Aug. 19, 2008

(54) ELECTRICAL CONDITION MONITORING METHOD FOR POLYMERS

(75) Inventors: Kenneth S. Watkins, Jr., Dahlonega, GA (US); Shelby J. Morris, Hampton, VA (US); Daniel D. Masakowski, Worcester, MA (US); Ching Ping Wong, Duluth, GA (US); Shijian Luo, Boise, ID (US)

(73) Assignee: Polymer Aging Concepts Inc., Dahlonega, GA (US)

( * ) Notice: Subject to any disclaimer, the term of this patent is extended or adjusted under 35 U.S.C. 154(b) by 108 days.

(21) Appl. No.: 10/506,518

(22) PCT Filed: Mar. 5, 2003

(86) PCT No.: PCT/US03/06844

§ 371 (c)(1),
(2), (4) Date: May 9, 2005

(87) PCT Pub. No.: WO03/076953

PCT Pub. Date: Sep. 18, 2003

(65) Prior Publication Data

US 2005/0268734 A1 Dec. 8, 2005

Related U.S. Application Data

(60) Provisional application No. 60/362,157, filed on Mar. 6, 2002.

(51) Int. Cl.
*G01N 17/00* (2006.01)
*G01N 33/44* (2006.01)
*G01N 27/04* (2006.01)
*G01N 27/20* (2006.01)
*G01R 31/12* (2006.01)

(52) U.S. Cl. .................. 324/693; 73/866; 324/71.1; 324/543

(58) Field of Classification Search ......... 73/865.9–866, 73/865.6, 786, 802; 324/543–544, 693, 691, 324/541, 555, 71.1
See application file for complete search history.

(56) References Cited

U.S. PATENT DOCUMENTS

| 3,603,142 | A |   | 9/1971  | Saylak et al.               |
|-----------|---|---|---------|-----------------------------|
| 4,520,341 | A | * | 5/1985  | Miyoshi et al. ....... 338/35 |
| 4,988,875 | A | * | 1/1991  | Ortiz et al. .......... 250/330 |
| 5,317,252 | A | * | 5/1994  | Kranbuehl ......... 324/71.1  |
| 5,432,435 | A | * | 7/1995  | Strong et al. ....... 324/71.1|
| 5,789,665 | A | * | 8/1998  | Voelker et al. ...... 73/53.05|
| 6,004,817 | A | * | 12/1999 | Chamberlain et al. ... 436/56 |
| 6,037,180 | A | * | 3/2000  | Yorkgitis et al. ..... 73/866 X|

(Continued)

FOREIGN PATENT DOCUMENTS

JP          361044339 A          3/1986

(Continued)

*Primary Examiner*—Thomas P. Noland
(74) *Attorney, Agent, or Firm*—Kenneth S. Watkins

(57) ABSTRACT

An electrical condition monitoring method utilizes measurement of electrical resistivity of an age sensor made of a conductive matrix or composite disposed in a polymeric structure such as an electrical cable. The conductive matrix comprises a base polymer and conductive filler. The method includes communicating the resistivity to a measuring instrument and correlating resistivity of the conductive matrix of the polymeric structure with resistivity of an accelerated-aged conductive composite.

45 Claims, 8 Drawing Sheets

U.S. PATENT DOCUMENTS

| | | | |
|---|---|---|---|
| 6,720,787 B2 * | 4/2004 | Kimura et al. | 324/765 |
| 6,802,446 B2 * | 10/2004 | Chaudhuri et al. | 228/248.1 |
| 6,810,718 B2 * | 11/2004 | Wilson et al. | 73/54.01 |
| 6,819,120 B2 * | 11/2004 | Tam | 324/693 X |
| 2005/0284232 A1 * | 12/2005 | Rice | 73/762 |
| 2007/0166831 A1 * | 7/2007 | Watkins et al. | 436/149 |

FOREIGN PATENT DOCUMENTS

WO     WO 2006091631 A2 *   8/2006

\* cited by examiner

ELECTRICAL CONDITION MONITORING METHOD FOR POLYMERS

This application claims priority for U.S. Provisional Application No. 60/362,157 filed Mar. 6, 2002.

This application resulted, in part, from research funded by the U.S. Department of Energy. Certain rights for any intellectual property resulting from this application may apply to the Government of the United States.

FIELD OF THE INVENTION

The present invention relates to methods and apparatus for determining deterioration and remaining life of polymeric material utilizing measured electrical quantities, and, more particularly, for determining mechanical properties and remaining life of a polymeric material by measurement of electrical resistivity of a conductive composite of the polymer.

BACKGROUND OF THE INVENTION

The polymeric materials used in wire and cable insulation and jacketing (and other polymers) degrade with age, especially in severe environmental conditions. The safe operation of existing and future plants such as nuclear power plants requires monitoring of the insulation materials in order to anticipate degradation before performance of the wire and cable is adversely affected.

Age related wire and cable failure is primarily a mechanical mechanism. As the insulation ages, it becomes embrittled and eventually fails mechanically by cracking and exposing bare conductors. The industry has spent considerable time and effort to develop condition monitoring methods which monitor installed wire and cable and ensure that the materials have not degraded excessively. These methods are also used to predict safe operating lifetime of wire and cable insulation materials for anticipated environmental conditions. Presently, cable condition monitoring (CCM) methods are categorized as mechanical methods, chemical methods and electrical methods.

Elongation-at-break (EAB) has traditionally been one of the most common and well-documented CCM methods. This mechanical method measures the elongation of a sample of insulation material just prior to break and is normally expressed as a ratio of the break length divided by the original length of the sample. Since elongation measured in the test is analogous to elongation occurring when bending wire and cable, the results can be easily correlated to actual wire and cable insulation condition. Arrhenius methods described by others are normally used to predict material lifetime at a target ambient temperature from acceleration-aged data.

A serious disadvantage of the EAB method is that a relatively large sample portion is required to perform the test. This makes the test essentially destructive since the cable is rendered inoperative when the sample is removed. Even if a cable is sacrificed in order to run a test, some portions of the cable may be difficult or nearly impossible to access for sample removal, as would be the case if the area of interest is within a cable bundle, wire tray, or internal to a penetration. The equipment needed for measurement is relatively expensive and requires specialized skills.

Indenter modulus test is a relatively new mechanical test that utilizes a machine to press a small anvil at constant velocity against the outer surface of the cable or insulated conductor while measuring the force exerted on the anvil. The indenter modulus is defined as the slope of the force-position curve. A major advantage of the indenter modulus test is that the test itself is non-destructive. However, the test is of limited use on conductor insulation since access to a sufficient length of individual conductors is often restricted. Also, the test is not practical on cable within cable bundles or trays, or in other confined spaces.

Oxidation Induction Time (OIT) is a chemical condition monitoring method that utilizes small (8-10 mg) samples removed from cable insulation materials. The method utilizes a differential scanning calorimeter (DSC) to provide an indication of the rapid oxidation of the sample when anti-oxidants, normally present in the insulation material, are exhausted. Short induction times indicate exhaustion of the anti-oxidant and anticipate rapid degradation of the material. Sample collection requires access to the cable which limits testable portions of the cable. Measurement requires expensive laboratory equipment and specialized training.

Electrical condition monitoring methods include insulation resistance, high potential tests, tan-delta tests, and ionized gas medium tests. These tests are essentially "go-no-go" tests (do not predict the remaining life of the sample) since no well-established methods reliably predict insulation lifetime based on the results. Several of these tests require high electrical potentials to be connected to cables, requiring removal of connected equipment and loads in order for the tests to be performed.

SUMMARY OF THE INVENTION

Therefore an object of the present invention is to provide a condition monitoring method for polymers which provides the ability to measure an electrical property of a conductive composite of the polymer in a non-destructive manner.

Another object of the invention is to provide a condition monitoring method which allows correlation of an electrical property of a conductive composite of the polymer with a mechanical property.

Another object of the invention is to provide a condition monitoring method which allows correlation of an electrical property of a conductive composite of the polymer with remaining life of the polymer.

Still another object of the invention is to provide a condition monitoring method which utilizes a conductive polymer tracer to monitor the aging conditions in any environment.

The methodology of the proposed condition monitoring method utilizes the electrical resistivity of a conductive composite formed from a candidate polymer material as a highly sensitive measurement of a mechanical property (volume shrinkage). Volume shrinkage, in turn, will be correlated as a mechanical indicator of insulation material aging. The method eliminates disadvantages of current methods and provides a condition monitoring method which improves safety and reduces condition monitoring costs.

The incorporation of inert conductive particles into the polymer to form a conductive composite provides several significant advantages for condition monitoring:

(1) A small change in volume of the conductive composite results in a large change in electrical resistivity. A few percent change in volume fraction of the insulation material provides a potential of 3-5 orders of magnitude or more change in the resistivity of the composite. This high measurement sensitivity provides an opportunity to detect and monitor small aging effects which current condition monitoring methods are insensitive to; and (2) Measurement of the electrical resistivity is a simple measurement requiring no special equipment, expertise or removal from service.

The conductive composite sensor may be distributed within a polymeric product such as electrical cables as a separate filament, or it could be co-extruded as a filament in the product.

BRIEF DESCRIPTION OF THE DRAWINGS

These and other features, aspects and advantages of the present invention will become better understood with regard to the following description, appended claims and accompanying drawings where:

DESCRIPTION OF THE PREFERRED EMBODIMENTS

Figure 1A:
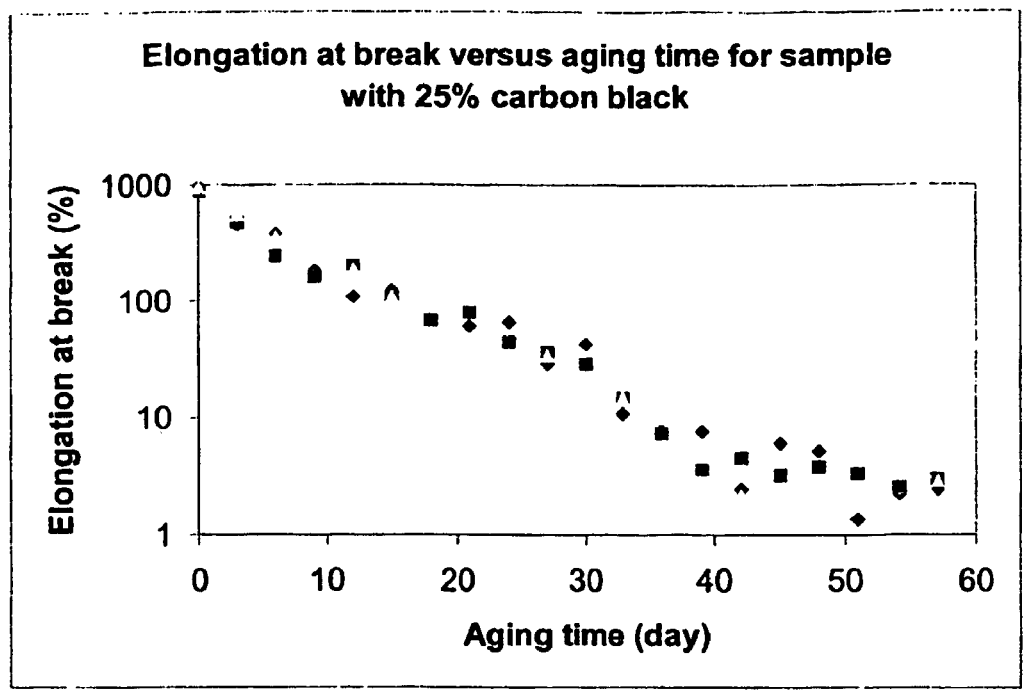
FIGS. 1A is a plot of elongation at break for a conductive composite sample of ethylene propylene rubber vs. age time at 125C.

The following is a description of the preferred embodiments of a method for determining the degradation of a polymeric material by use of an electrical measurement.

Definitions: Although the term resistivity (electrical) is used throughout the specification, it is understood that conductivity, as the reciprocal of resistivity, can be substituted as a measurable electrical property by those skilled in the art.

The term conductive composite polymer, as used in this specification, is generally meant to include any conductive composite comprising a mixture of conductive particles in a polymer matrix or base, and may include additional fillers, additives and binders. This composite type conductive polymer is differentiated from intrinsically conductive polymers which posses electrically conductive properties without addition of conductive particles.

The method of the present invention utilizes measurement of an electrical property of a conductive composite to indirectly measure the aging or degradation effects on a polymeric material. In the preferred embodiments, the conductive composite comprises conductive particles such as carbon black particles or metallic particles evenly dispersed or mixed in the polymeric material of interest. Degradation and aging effects which include chain scission and additional cross-linking will result in volumetric changes to the polymeric portion of the composite and will affect electrical properties such as the resistivity or conductivity of the composite.

Degradation and aging mechanisms of polymers are numerous and complex, but cross-linking of polymer chains, caused by thermal exposure, radiation exposure, and thermal-oxidative mechanisms has been shown in the literature to result in increased packing density of the polymer chains, resulting in densification and volumetric shrinkage. If conductive fillers are chosen which are relatively inert for the environments in which the composites are used and tested, the volume fraction of the filler will remain constant with degradation of the polymer matrix. The resulting volumetric shrinkage of the polymer matrix of a conductive composite results in an increase in the volume fraction of the conductive filler particles in the composite.

Changes in the volume fraction of conductive fillers can be detected by electrical measurements of the conductive composite. Specifically, the resistivity (or conductivity) provides a measure of the volume fraction of the conductive filler.

Resistivity measurements of conductive composites affords very high sensitivity to conductive filler volume fraction changes in conductive polymer composites as a result of polymer matrix shrinkage and densification. For example, the volumetric shrinkage of a polymer due to age-related cross-linking may be on the order of only a few percent over the useful life of the polymer. Selection of the conductive filler type and loading may result in several orders of magnitude of resistivity change due to the volumetric shrinkage. This is especially the case if the conductive filler loading is chosen to be in the percolation zone of the conductive composite. Other aging mechanisms, such as loss of volatile components of the polymer during aging also result in an increase in the volume fraction of the conductive filler.

The high sensitivity of resistivity of a conductive polymer composite to volumetric shrinkage (or expansion) of the polymer matrix provides an amplified method useful in detecting an measuring the small changes in polymer volume fraction as a result of age-related degradation such as cross-linking of the matrix due to thermal, radiation, and thermal oxidative mechanisms. While direct measurements of volumetric shrinkage of the polymers would provide a quantitative means to detect degradation, this method is usually destructive for many applications, and requires laboratory analysis. Measurement of resistivity, although an indirect measurement of the volumetric shrinkage, provides a non-destructive, in-situ, measurement that is much more sensitive than can be done by normal laboratory measurements of volumetric shrinkage or density, and can be carried out with simple field equipment such as an ohmmeter or multimeter.

The amplifying effect of the conductive composite resistivity measurement approach allows measurement of volumetric or density changes smaller than that afforded by direct mechanical measurements. For example physical aging effects, such as relaxation of polymer chain networks of polymers below the glass transition temperature, and creep effects can be detected over short time intervals by resistivity measurements of conductive composites of the polymer. Detection of natural aging effects over short time periods, such as days or weeks is possible by this method, where months or years would be required by conventional mechanical or chemical measurements such as elongation to break, and oxygen induction time (OIT) measurements.

EXAMPLES

Figure 1B:
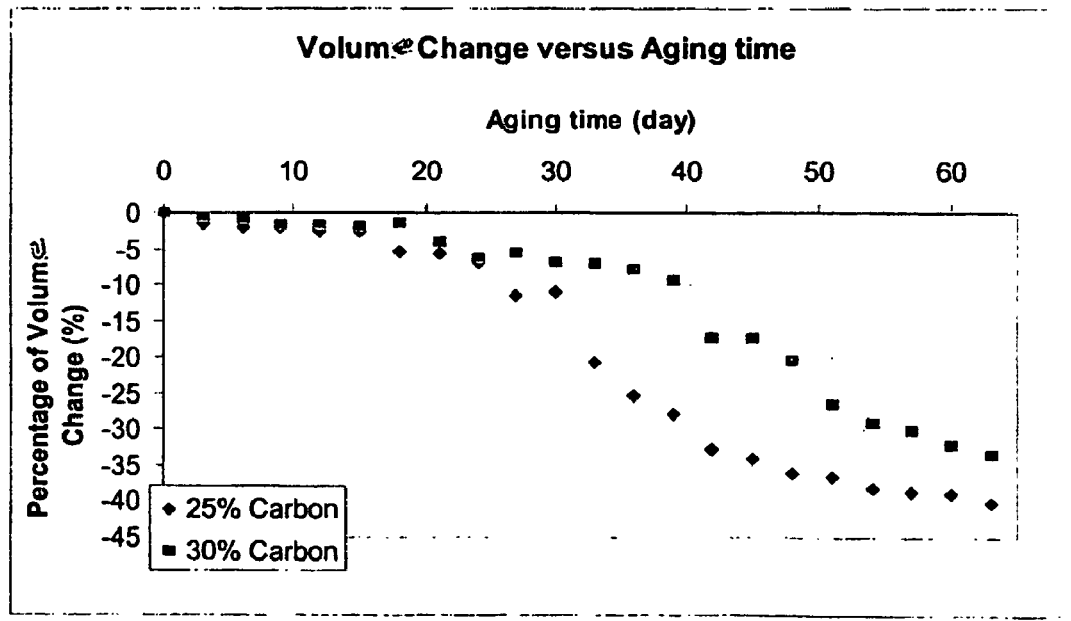
FIG. 1B is a plot of volume change (shrinkage) for a conductive composite sample of ethylene propylene rubber vs. age time at 125C.
Figure 1C:
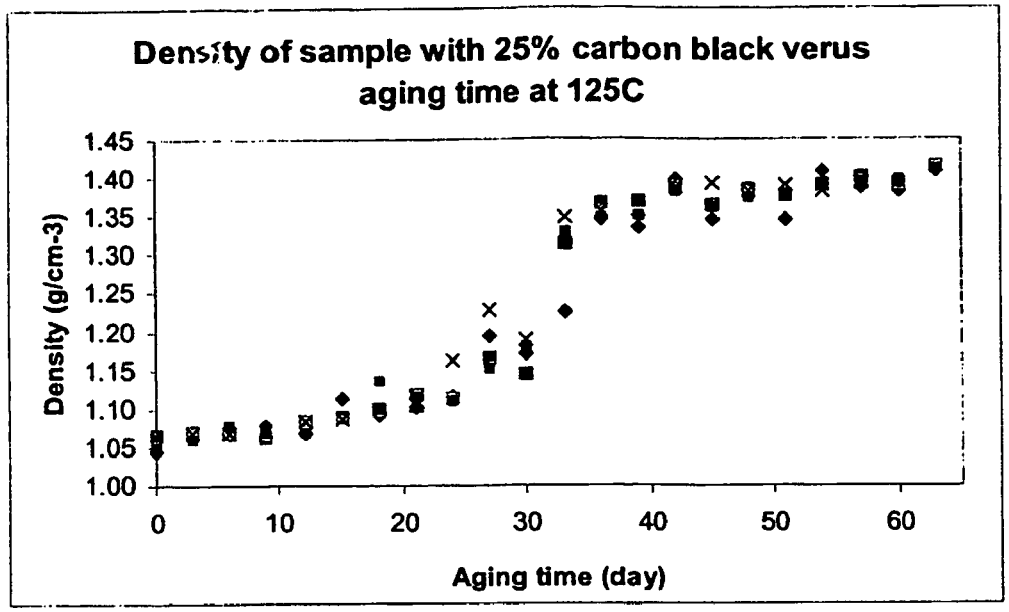
FIG. 1C is a plot of density of a conductive composite sample of ethylene propylene rubber vs. age time at 125C.
Figure 1D:
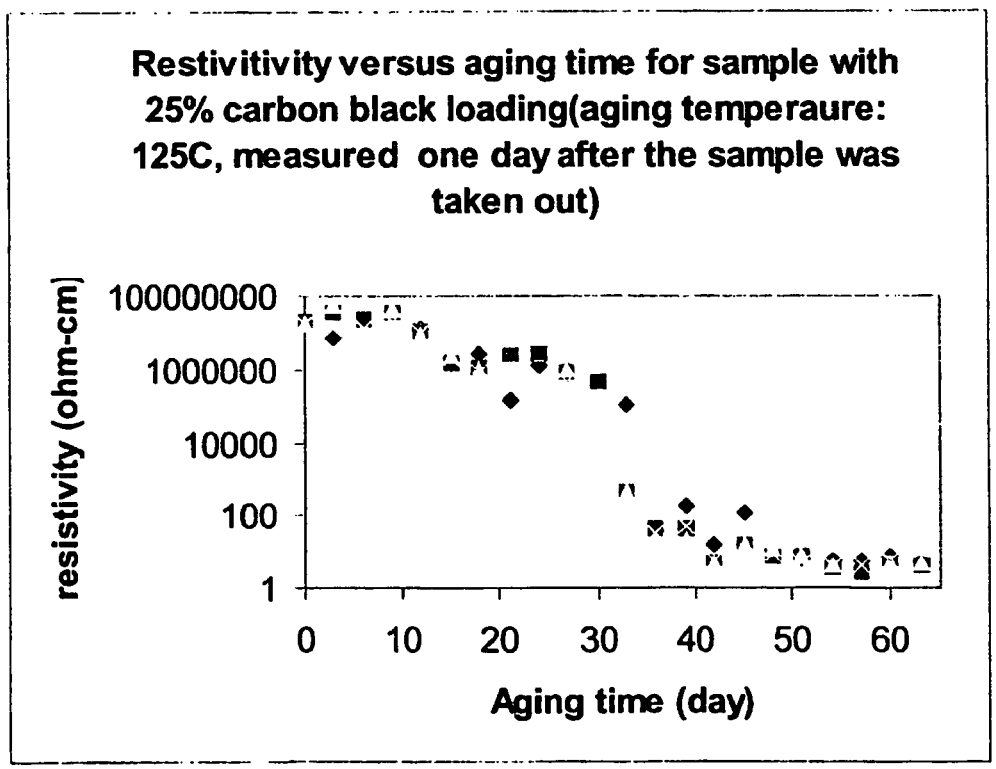
FIG. 1D is a plot of electrical resistivity of a conductive composite sample of ethylene propylene rubber vs. age time at 125C.

FIGS. 1A, 1B, and 1C show elongation at break, volume change and density of ethylene propylene rubber (EPR) under accelerated thermal aging at 125C. FIG. 1D shows resistivity change for EPR samples under the same aging conditions.

Use of resistivity data of polymeric composite materials could be used in several ways. For example, accelerated aging of a composite comprising a specific polymer and a given volume fraction of a conductive filler would result in a resistivity vs. time for the test temperature. Measurement of mechanical properties such as elongation at break or hardness as the composite is aged, would provide a relationship of the mechanical property to the resistivity for the composite. This relationship could be determined by the aging curves, such as that of FIGS. 1A, 1B, 1C and 1D showing the value of the mechanical property vs. resistivity. Or, the relationship could be expressed by a mathematical algorithm by curve fitting methods known in the art. By inclusion of base polymer samples (without conductive fillers) during the aging trial, the mechanical properties of the base polymer could be predicted by measurement of a representative sample of the conductive composite having the same base polymer.

By incorporating aging trials of a conductive composite at several temperatures, measuring resistivity and mechanical properties vs. aging time, Arrhenius methodology and/or time/temperature superposition known in the art could be used to predict remaining lifetime of the composite (or base polymer) as a function of aging temperature. In-situ measurement of the resistivity of a test or trial portion of the polymer having conductive filler could be used to verify the remaining life of the polymer and act as an indirect measurement of desired mechanical properties.

Physical aging affects of polymers could be modeled in a similar means by thermal processing a conductive composite, optionally in an inert gas environment, and measuring resistivity vs. mechanical properties such as volumetric shrinkage, density and creep properties.

Figure 2A:
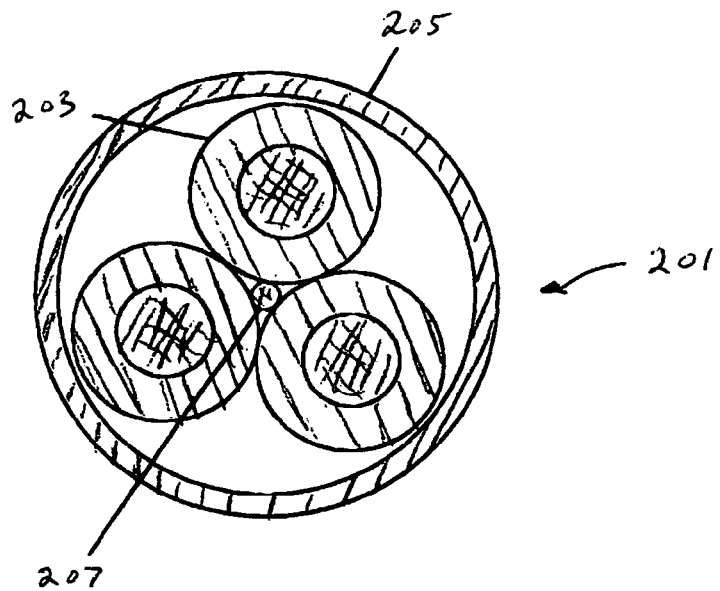
FIG. 2A is a cross section of an electrical cable comprising an age sensor filament made of a conductive composite.

FIG. 2A is a cross section of a multi-conductor cable 201 having three insulated conductors 203, an outer cable jacket 205, and an age sensor filament 207 disposed in the cabled conductors. In the preferred embodiments, the age sensor filament "tracer" is a conductive composite comprising the conductor insulator polymer as the base polymer and conductive filler such as carbon black. In other embodiments, the conductive composite utilizes a second polymer as the base polymer. In still other embodiments, the conductive composite utilizes metallic or metallic oxides as the conductive filler. The sensor filament may be positioned at other locations in the cable such as outside the insulated conductors and inside the cable jacket.

Figure 2B:
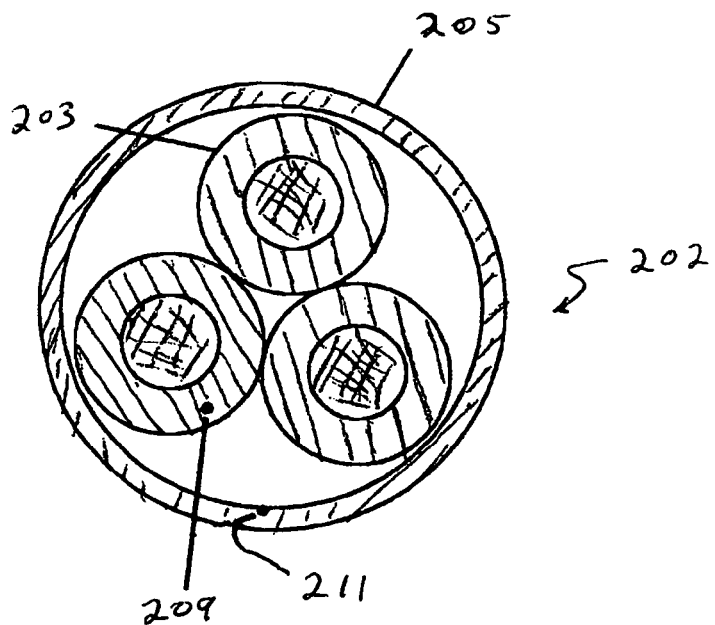
FIG. 2B is a cross section of an electrical cable comprising an age sensor filament co-extruded in an insulated conductor insulation and a cable jacket.

FIG. 2B is an alternative embodiment 202 of the cable of FIG. 1 utilizing a co-extruded age sensor tracer 209 in the insulated portion of the insulated conductor, or an alternative age tracer 211 co-extruded in the cable jacket. In the preferred embodiments, the base polymer of the senor tracers is the same polymer as the insulated conductor or jacket. In other embodiments, a different base polymer is utilized.

Figure 3:
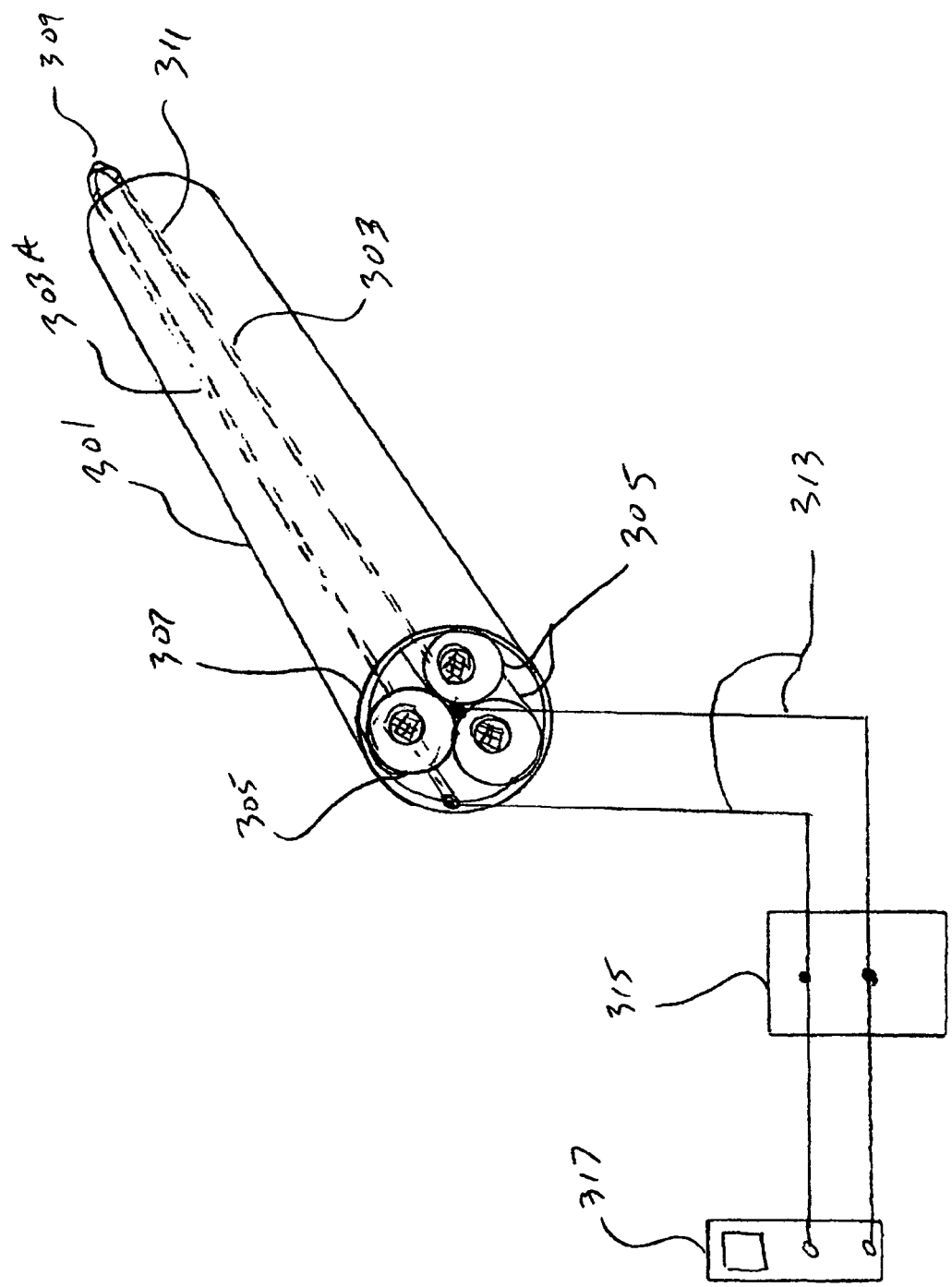
FIG. 3 is a schematic diagram of a means for measuring the resistivity of a conductive age sensor filament.

FIG. 3 is a schematic of a method of monitoring the resistivity of the age sensor 303 of cable 301. Age sensor filament 303 is distributed along the cable and disposed, for example, along the insulated conductors 305. A second element 303A, is disposed along the length of cable 301 inside jacket 307. Second element 303A may be another age sensor filament similar to age sensor filament 303, or it may be an insulated or non-insulated conductor such as a metallic conductor. Shunt 309 connects age sensor 303 and second element 303A to form a series-connected loop 311 which functions as an electrical age sensor for the cable. Conductors 313 connect age sensor loop 311 to terminal box 315. A resistance-measuring instrument, such as ohmmeter 317 measures the resistance of age sensor loop 311 at terminal box 315. By monitoring resistance (or resistivity calculated from the sensor dimensions) changes in age sensor loop 311 and comparing the results to accelerated aged conductive composites and insulation base polymers, the material properties such as elongation-at-break of the insulation polymers may be determined.

In other embodiments ohmmeter 317 connects directly to age sensor 303 and second element 303A.

Figure 4:
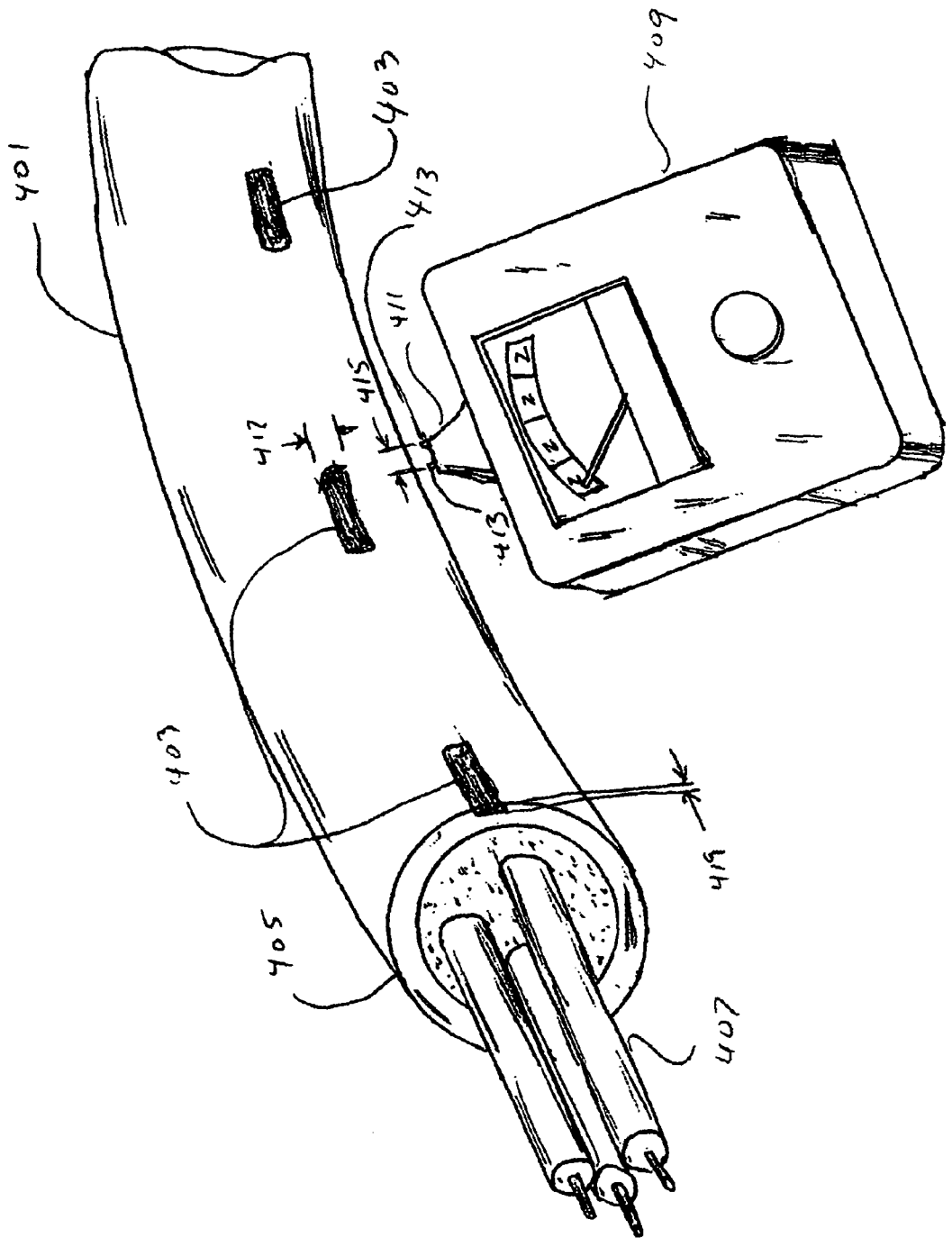
FIG. 4 is a perspective drawing of an electrical cable comprising a plurality of age sensors disposed in the cable jacket.

FIG. 4 is a perspective drawing of an alternative method of monitoring cable condition. Cable 401 comprises a plurality of condition or age sensors 403 embedded in cable jacket 405. Age sensors 403 may be a conductive composite of cable jacket 405 or insulated conductor 407 polymers co-extruded in jacket 405. In other embodiments, conductive composites utilized in age sensors 403 may be made of other polymers designed to degrade in a manner similar to insulated conductors 407 or jacket 405.

A composite condition or age sensing instrument such as ohmmeter 409 may comprise a probe 411 having terminals 413 spaced to provide a resistivity measurement of age sensors 403 when contacted with age sensor 403. Terminals 413 comprise a predetermined spacing 415 to provide a resistivity reading of age sensors 403 which comprise a predetermined width 417 and predetermined thickness 419.

Figure 5:
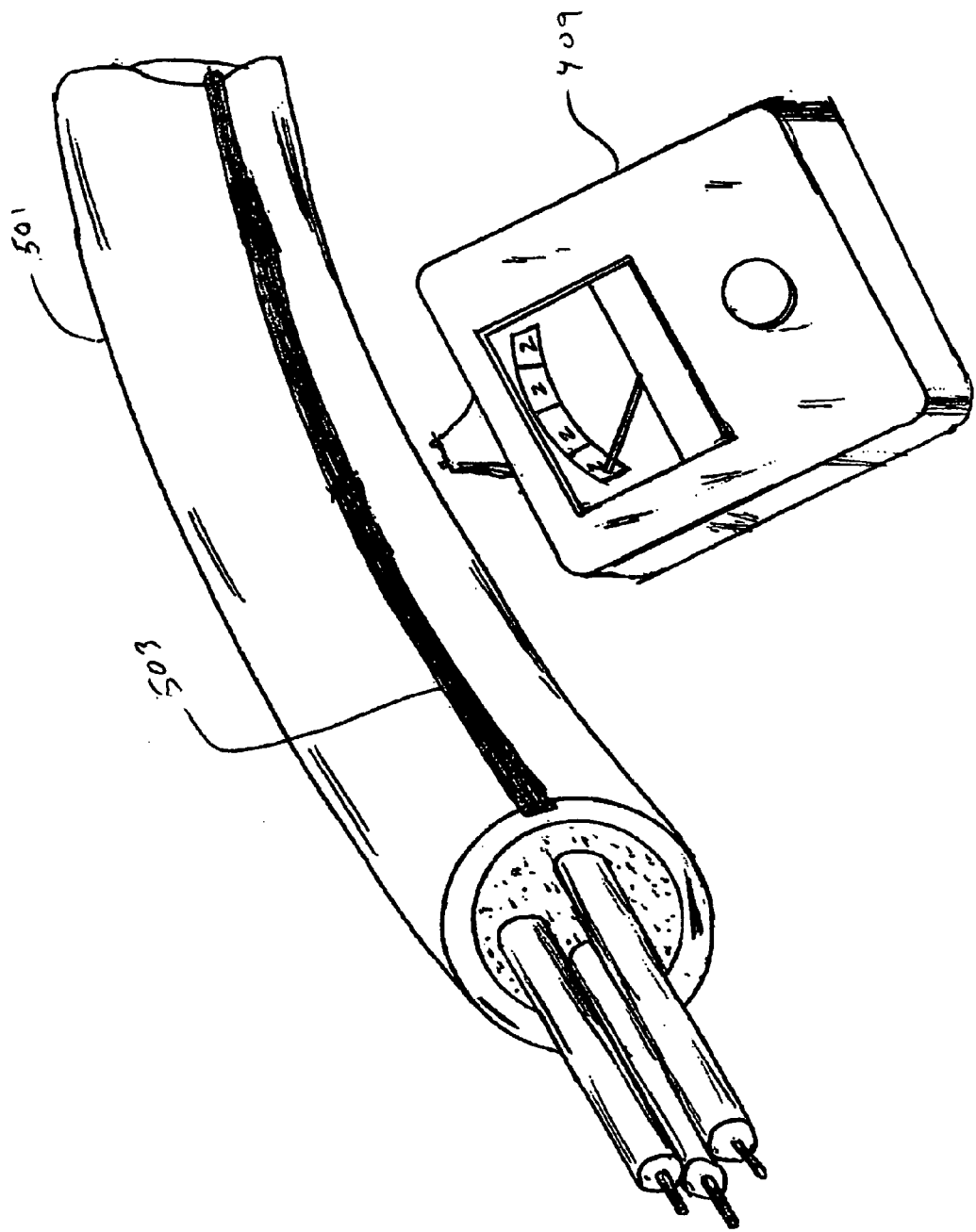
FIG. 5 is a perspective drawing of an electrical cable comprising an age sensor strip disposed in the cable jacket.

FIG. 5 is an alternative embodiment 501 of the cable of FIG. 4 having a continuous condition/age sensor strip 503. Sensor strip 503 comprises a predetermined width and thickness similar to age sensors 403 of FIG. 4.

Figure 6:
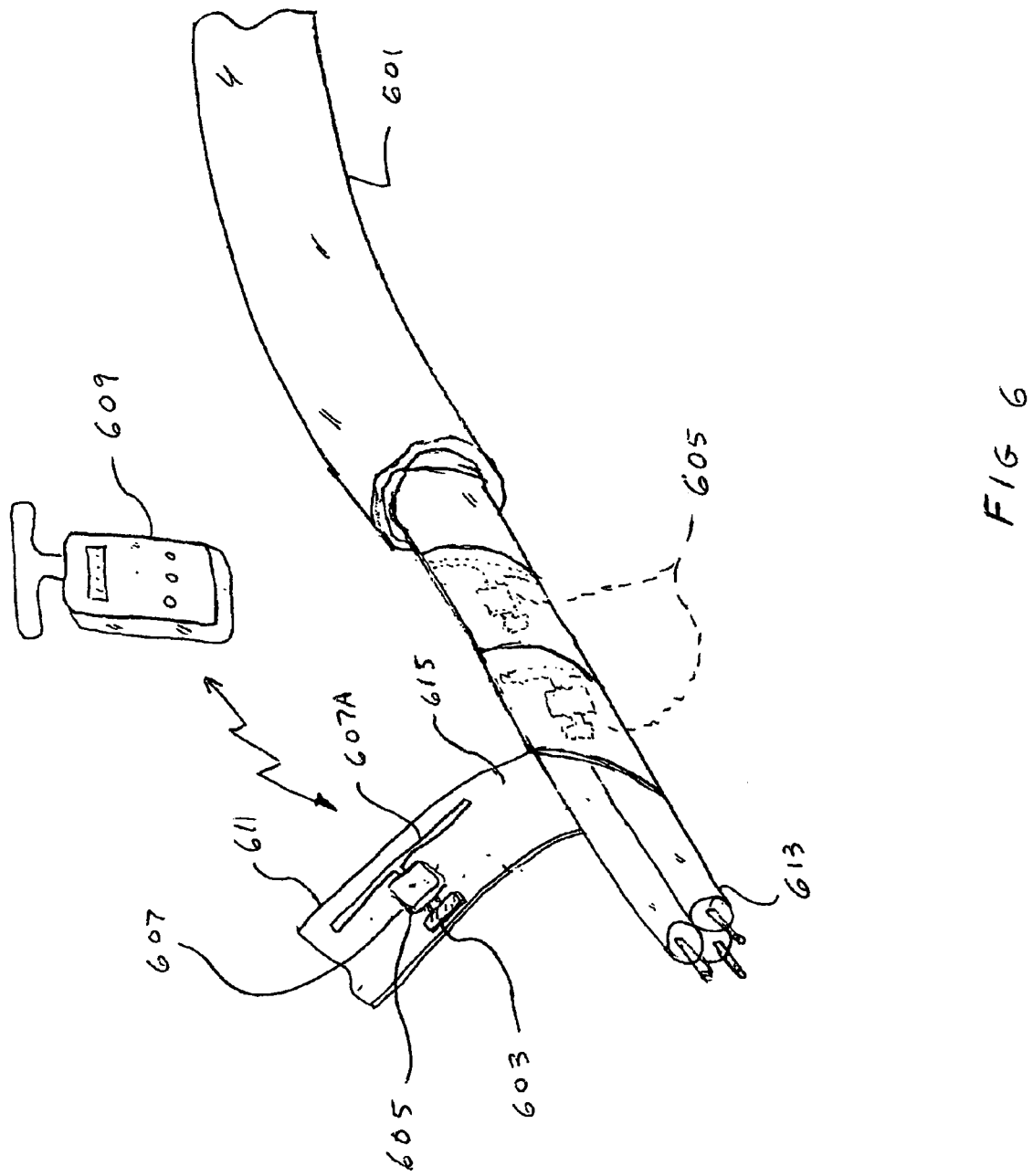
FIG. 6 is a perspective drawing of a plurality of age sensor assemblies utilizing an RFID to communicate resistivity to an external instrument.

FIG. 6 is an embodiment of another method of monitoring age sensors 603 of cable 601 by utilizing radio frequency identification (RFID) tag assemblies 605. Tag assemblies 605 comprise age sensors 603 made from a conductive composite connected to an RFID chip 607. RFID chip 607 may comprise an antenna 607A for active or passive communication with a reader 609. A plurality of tag assemblies 605 may disposed in cable 601, for example by attaching assemblies 605 to tape 611 and wrapping tape 611 around insulated conductors 613. Tape 611 may comprise an adhesive surface 615 for retaining tag assemblies 605. In still other embodiments, a RFID tag assembly 605 may be connected to sensor loop 311 of cable 301 of FIG. 3 and embedded in cable 301.

Figure 7:
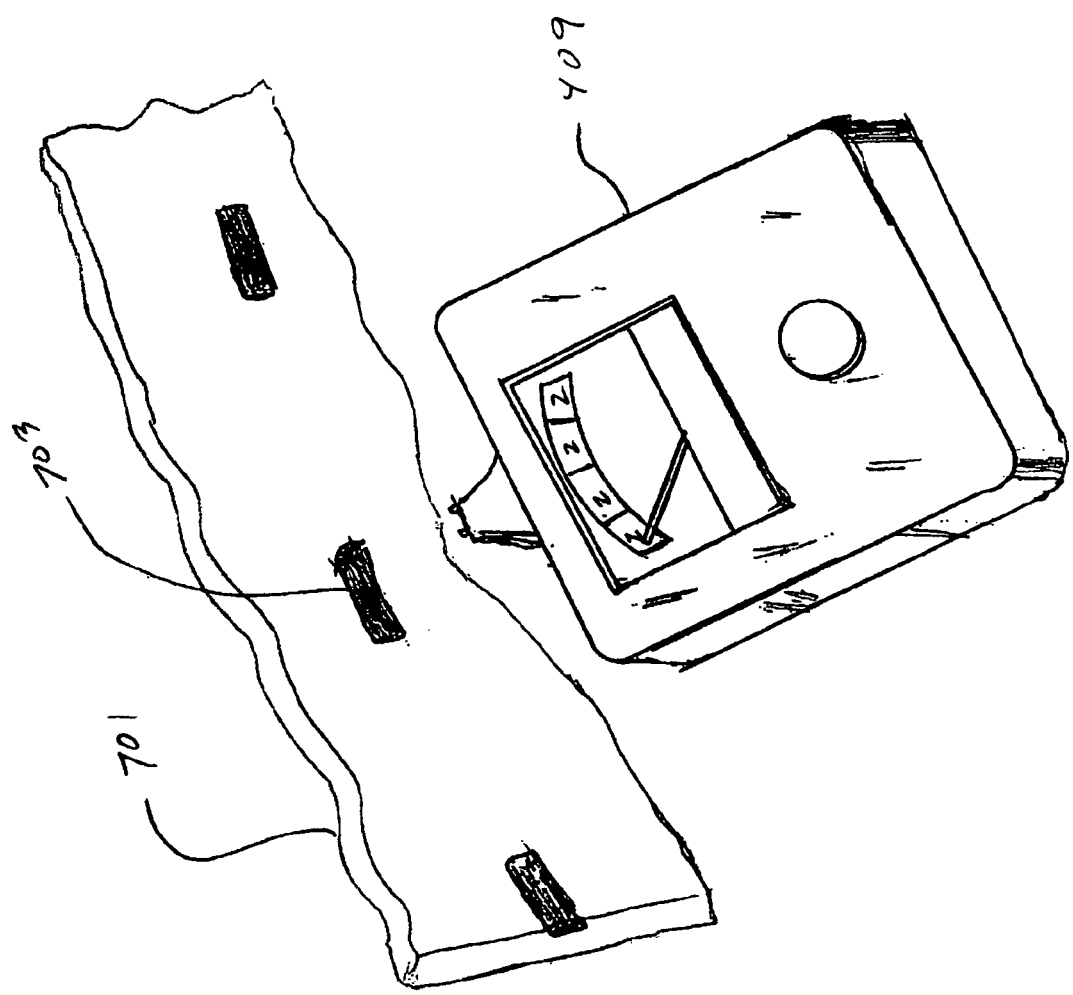
FIG. 7 is a perspective drawing of a polymeric structure comprising a plurality of conductive composite age sensors disposed in the structure.
Figure 1A:
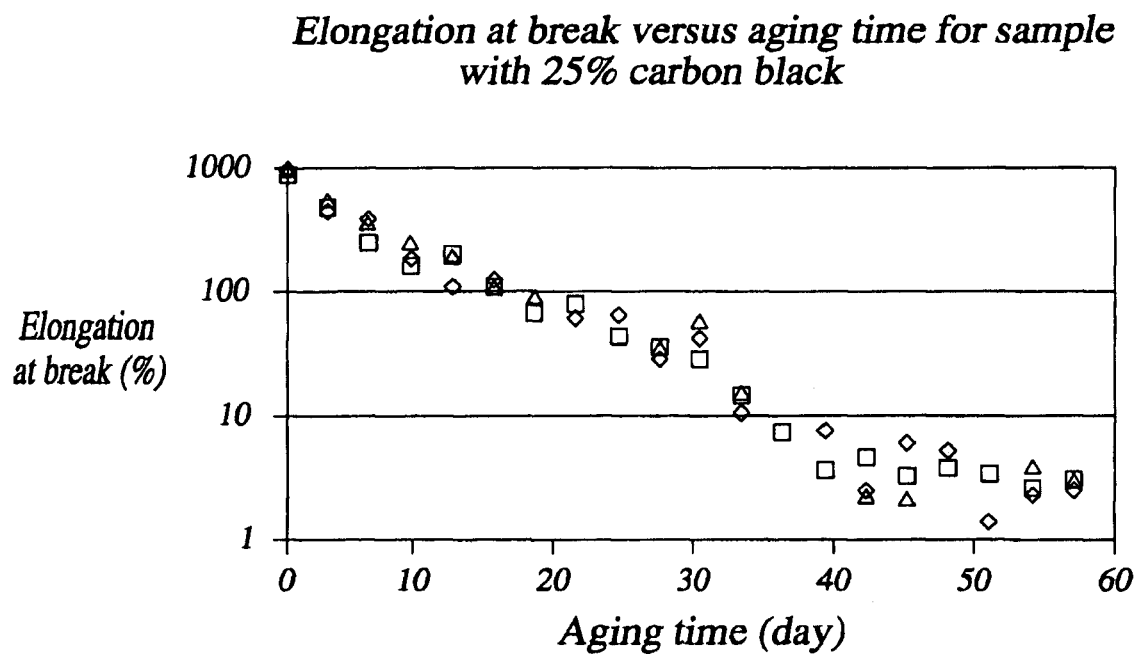
Figure 1B:
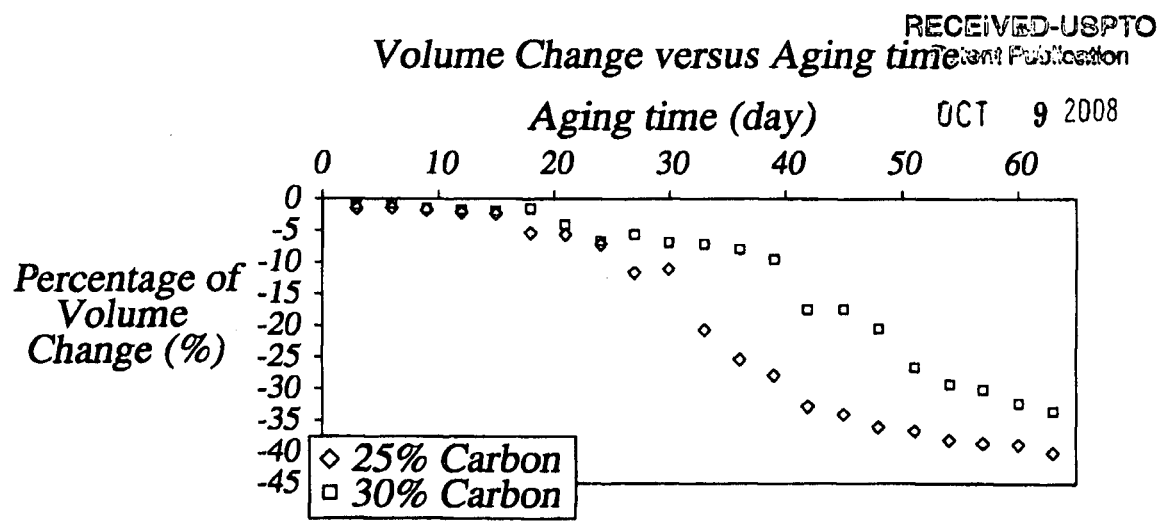
Figure 1C:
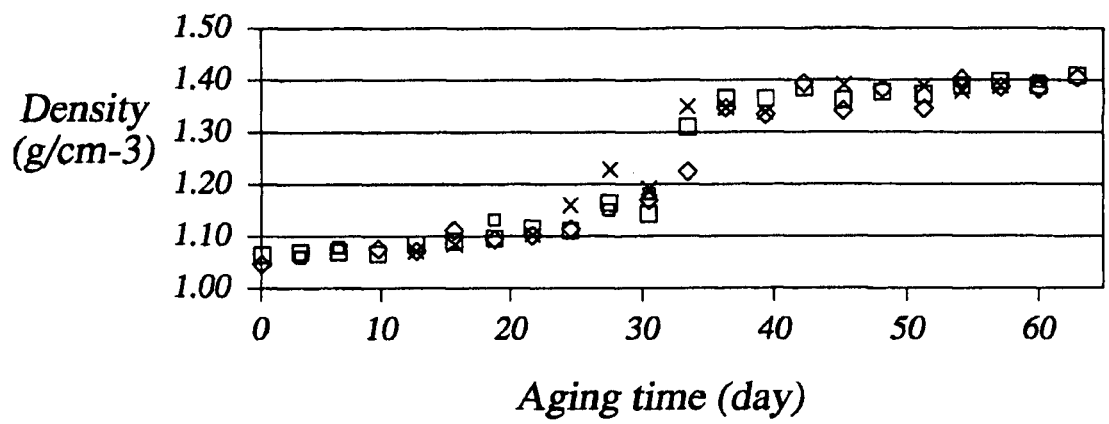
Figure 1D:
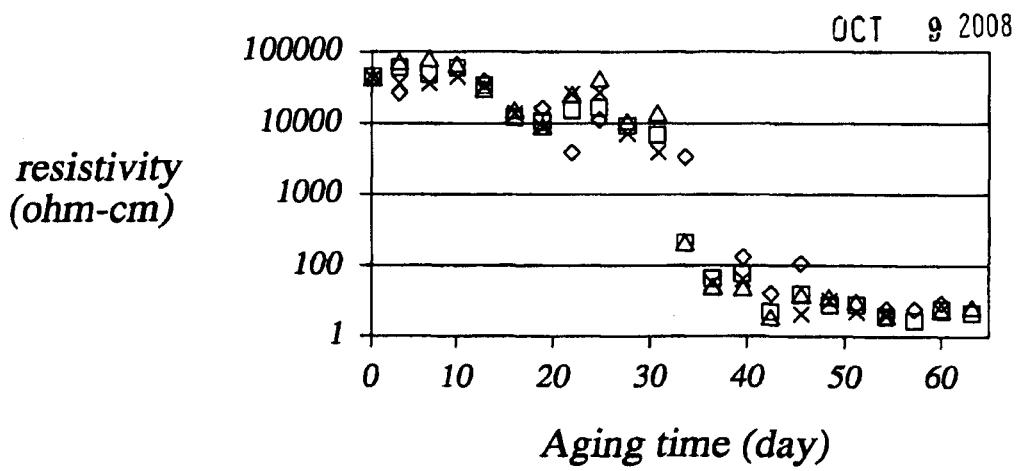
Figure 2A:
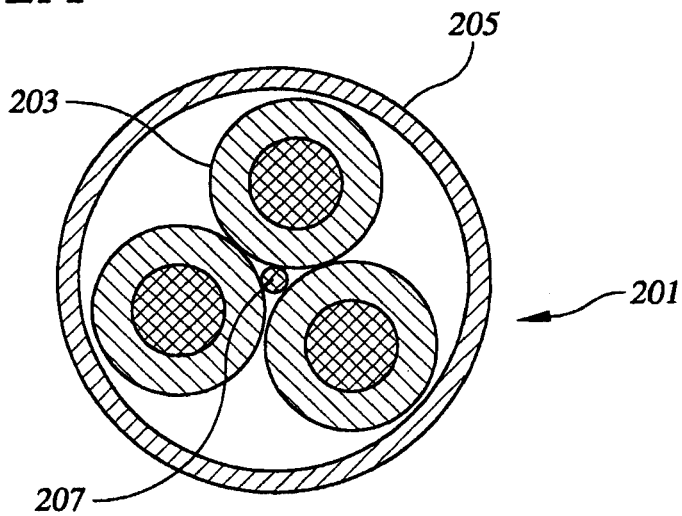
Figure 2B:
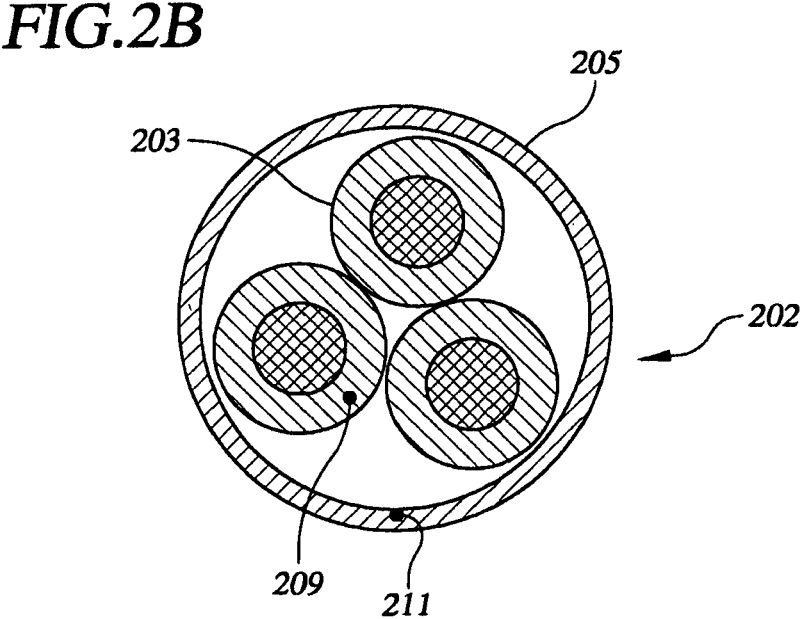
Figure 3:
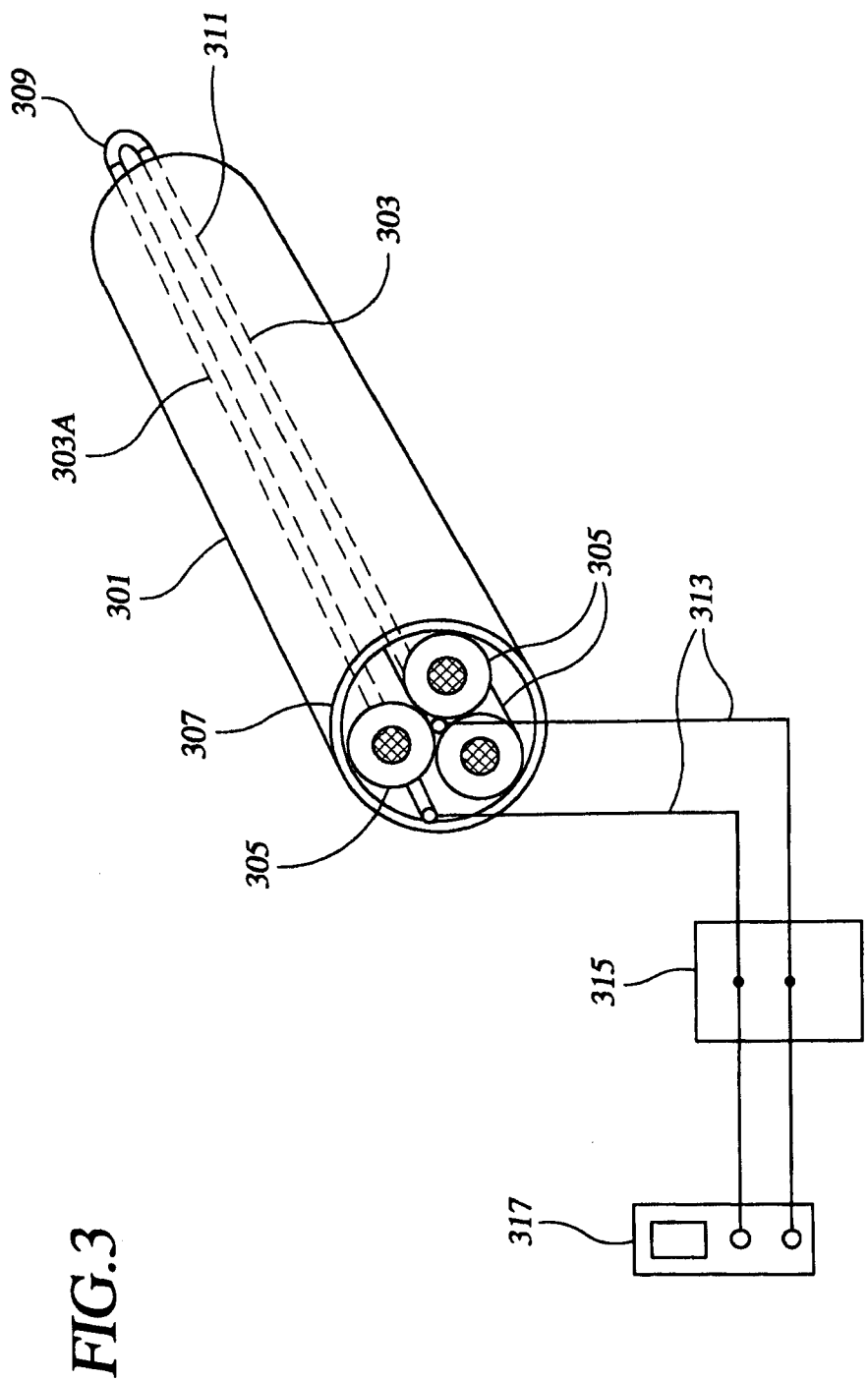
Figure 4:
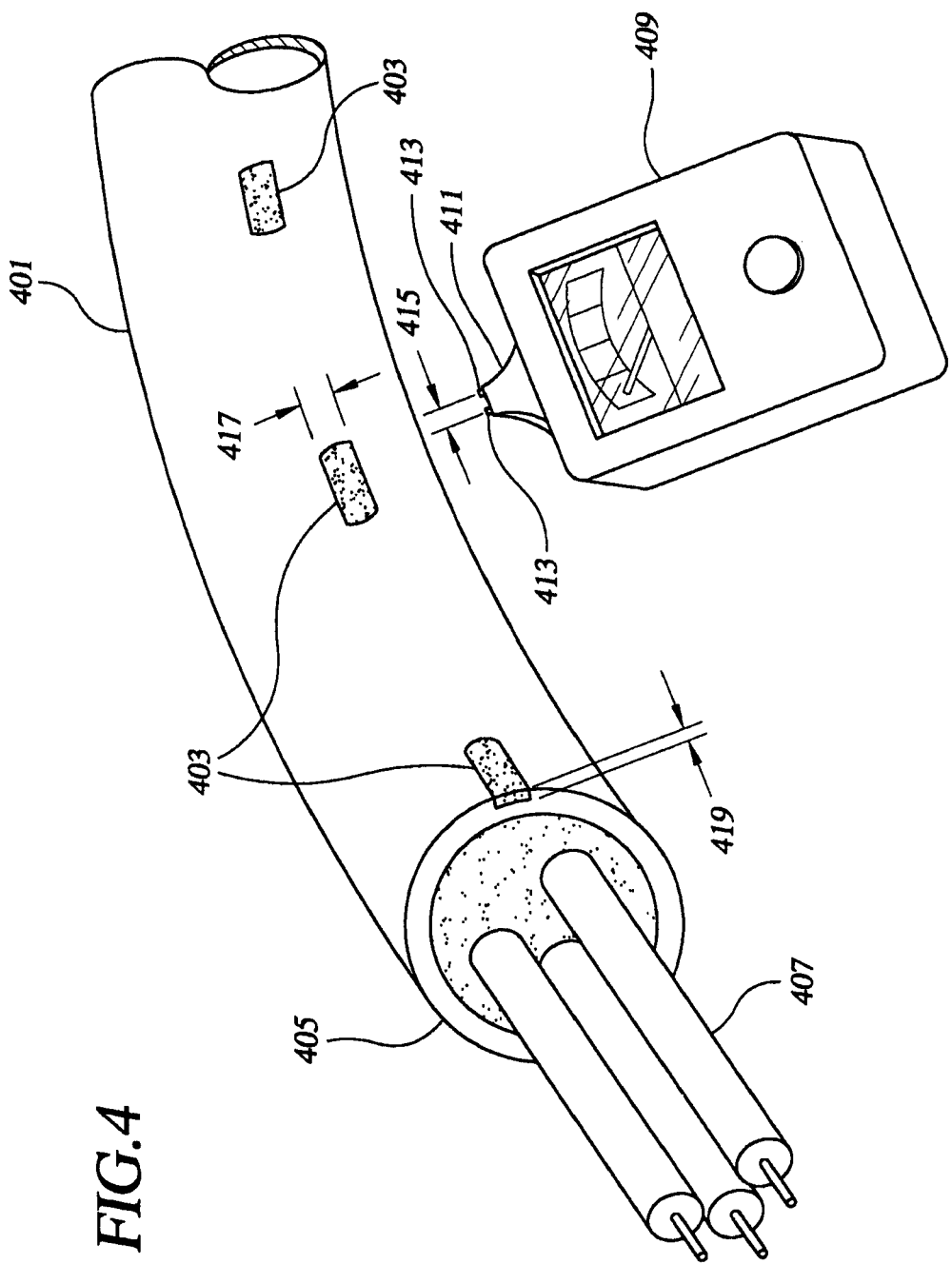
Figure 5:
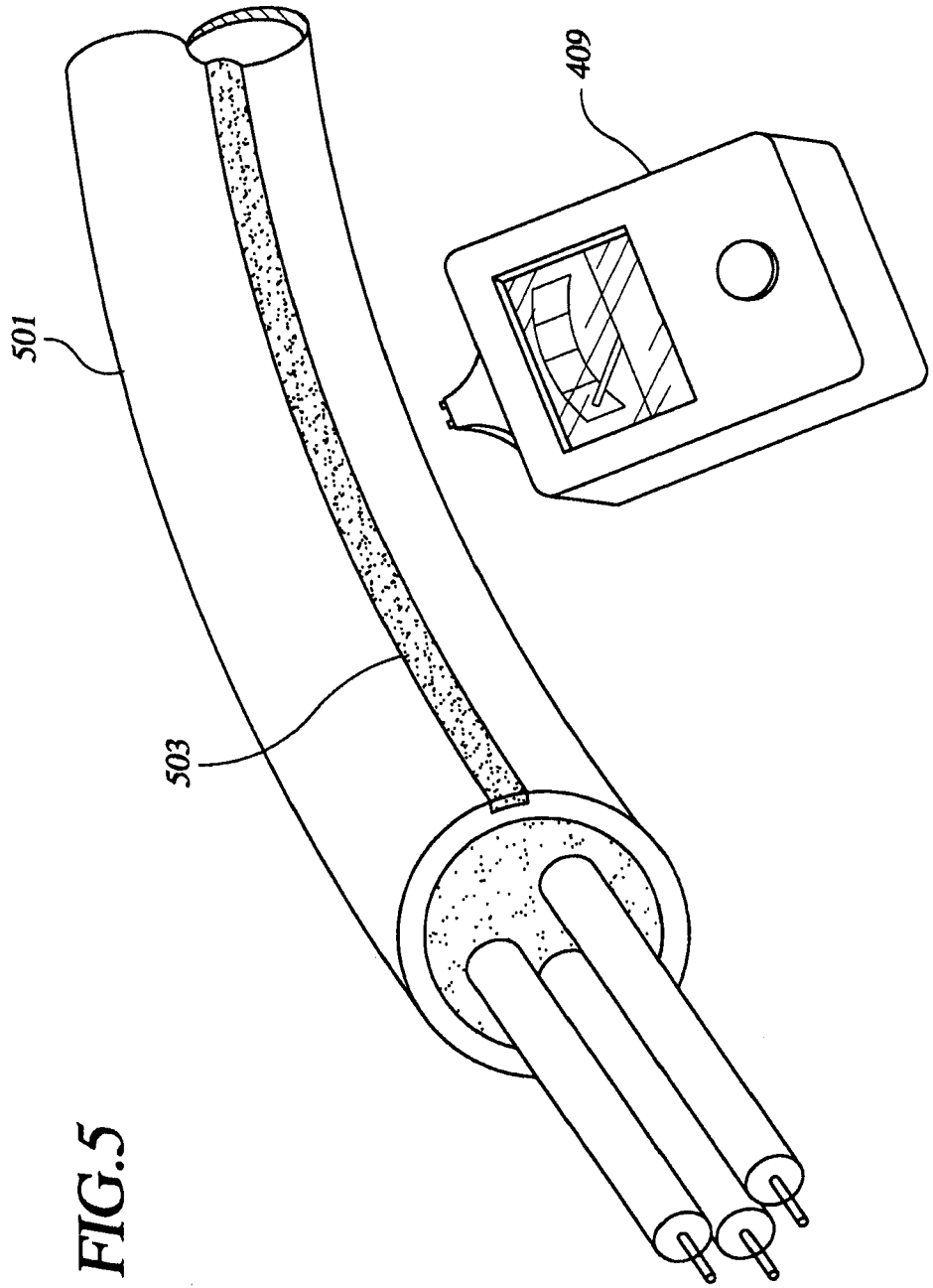
Figure 6:
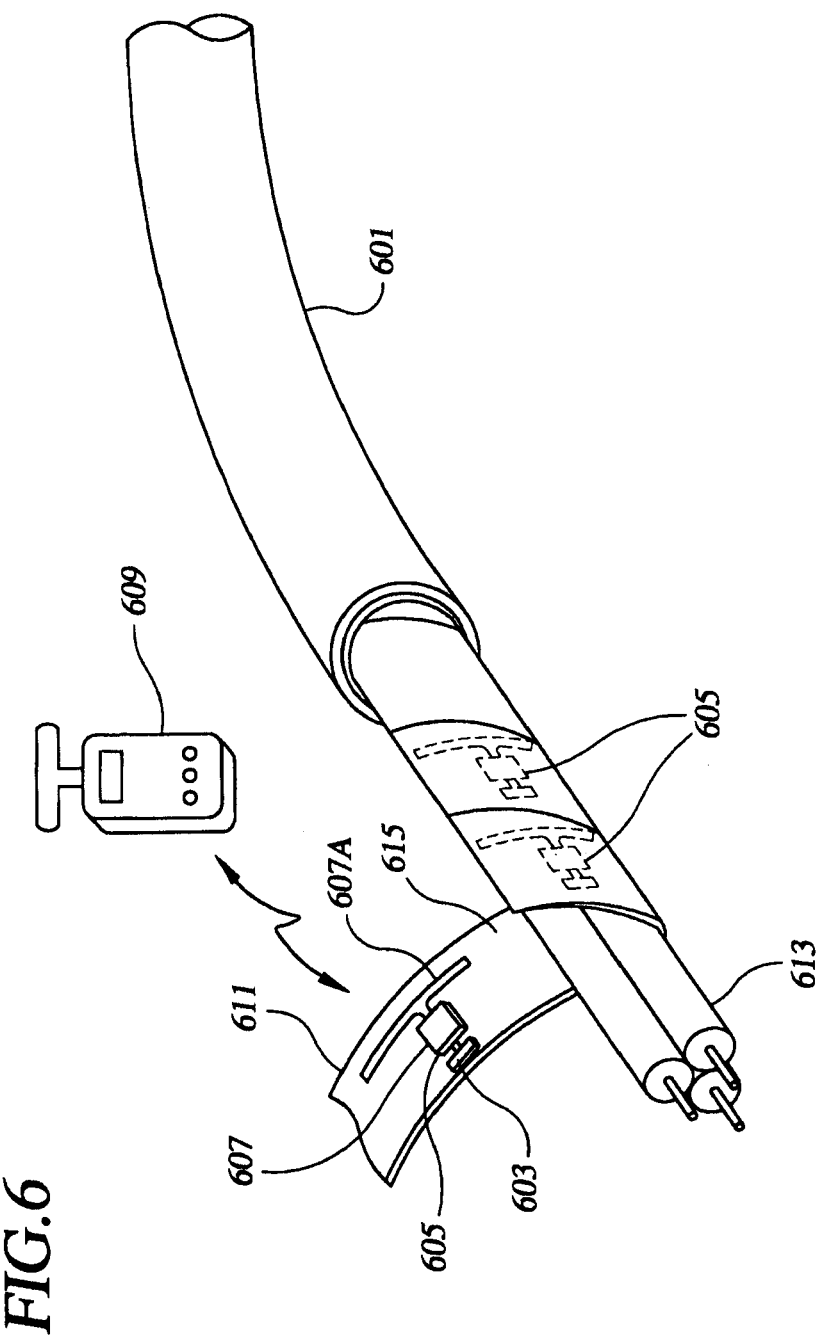
Figure 7:
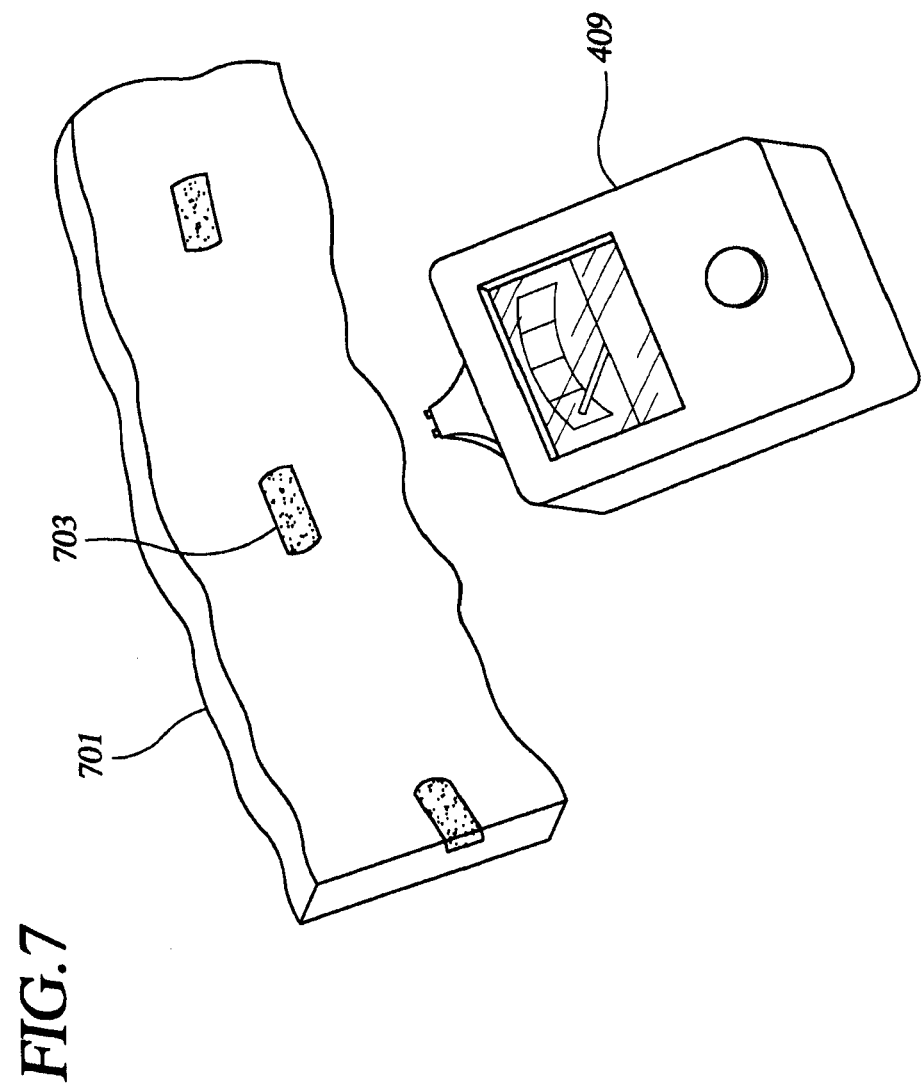

FIG. 7 shows the method of FIG. 4 applied to other extruded or cast polymer products 701 such as extruded or cast polymer siding, extruded or cast polymer pipe or tube, extruded, cast or laid-up composite structures such as aircraft structural parts and boat hulls. Age/condition sensors 703 are made from conductive composites as discussed in previous examples, and may be co-extruded, cast, or they may be applied as conductive hot-melt or adhesive composites. Continuous age sensor strips such as strip 503 of FIG. 5 may be substituted for age sensors 703.

In the preferred embodiments, age sensor conductive composites utilize the base polymer of the structure they are monitoring, such as the insulation polymer for wire and cable age sensors, or PVC for house siding. In some embodiments, the age sensor composite may be "designed" to age at the same, or in some cases faster than the base polymer by altering the filler content, adding or deleting anti-oxidants to the age sensor, or "pre-aging" the age sensor by accelerated aging techniques to match aging performance with the polymeric structure being monitored. These techniques may also be used to alter the response of the age sensor to more nearly follow natural aging of the polymer.

Although the description above contains many specifications, these should not be construed as limiting the scope of the invention but merely providing illustrations of some of the presently preferred embodiments of this invention. Thus the scope of the invention should be determined by the appended claims and their legal equivalents, rather than by the examples given.

We claim:

1. A method of determining environmentally induced degradation of a polymer, the method comprising the steps of:
   adding conductive particles to the polymer to form a conductive composite comprising a preselected weight percent of conductive particles;
   making an electrical connection with the conductive composite and measuring an electrical property of the conductive composite; and
   equating a change in the electrical property of the conductive composite, with the same electrical property of a previously environmentally degraded sample of the conductive composite to determine the degradation of the polymer, the change in the electrical property consistent with a decrease in electrical resistivity.

2. The method of claim 1 wherein the measured electrical property is electrical resistivity.

3. The method of claim 1 wherein the measured electrical property is electrical conductivity.

4. The method of claim 1 wherein the degradation of the polymer is mechanical degradation of the polymer.

5. The method of claim 4 wherein the mechanical property comprises a durometer of the polymer.

6. The method of claim 4 wherein the mechanical property comprises an elongation property of the polymer.

7. The method of claim 4 wherein the mechanical property comprises a hardness of the polymer.

8. The method of claim 4 wherein the mechanical property comprises a tensile strength of the polymer.

9. The method of claim 4 wherein the mechanical property comprises a toughness of the polymer.

10. The method of claim 1 wherein the degradation of the polymer is a chemical degradation.

11. The method of claim 10 wherein the chemical degradation comprises a measure of oxidation of the polymer.

12. The method of claim 10 wherein the chemical degradation comprises a measure of a remaining amount of antioxidant added to the polymer.

13. The method of claim 1 wherein the previously degraded sample was degraded by an accelerated aging means.

14. The method of claim 13 wherein the accelerated aging means comprises aging in an environment elevated in temperature as compared to the normal operating temperature of the polymer.

15. The method of claim 13 wherein the accelerated aging means comprises aging in an elevated radiation environment.

16. The method of claim 13 wherein the accelerated aging means comprises aging in an elevated humidity environment.

17. A degradation sensor for a polymeric structure, the sensor comprising:
   a first quantity of conductive particles dispersed in a first portion of the polymeric structure to define a conductive composite portion, the first portion comprising less than a total polymer in the structure; and
   a means for communicating an electrical measurement of the conductive composite to an electrical measurement apparatus; and
   a means for correlating a decrease in said electrical measurement consistent with a decrease in resistivity to an environmentally induced degraded condition of said polymeric structure.

18. The degradation sensor of claim 17 wherein the means for communicating an electrical measurement of the conductive composite comprises a portion of the conductive composite disposed on an outside surface of the polymeric structure.

19. The degradation sensor of claim 17 wherein the means for communicating an electrical measurement of the conductive composite comprises a metallic conductor communicating with the conductive composite.

20. The degradation sensor of claim 17 wherein the means for communicating an electrical measurement of the conductive composite comprises an electromagnetic emitter.

21. The degradation sensor of claim 20 wherein the electromagnetic emitter is a radio frequency identification tag.

22. The degradation sensor of claim 17 wherein the conductive composite defines a filament disposed in the polymeric structure.

23. The degradation sensor of claim 17 wherein the conductive composite defines an extruded strip in the polymeric structure.

24. The degradation sensor of claim 17 wherein the conductive composite defines a plurality of portions of conductive composite, said plurality of portions of conductive composite being separated from each other by portions of polymer without said conductive particles.

25. A polymeric structure comprising:
   a degradation sensor for the polymeric structure, the sensor comprising:
   a first quantity of conductive particles dispersed in a first portion of the polymeric structure to define a conductive composite portion, the first portion comprising less than a total polymer in the structure; and
   a means for communicating an electrical measurement of the conductive composite to an electrical measurement apparatus; and
   a means for correlating a decrease in said electrical measurement consistent with a decrease in resistivity to an environmentally induced degraded condition of said polymeric structure.

26. The polymeric structure of claim 25 wherein the polymeric structure is the insulation of an electrical wire.

27. The polymeric structure of claim 25 wherein the polymeric structure is an electrical cable.

28. The polymeric structure of claim 25 wherein the polymeric structure is a pipe.

29. The polymeric structure of claim 25 wherein the polymeric structure is a building siding portion.

30. The polymeric structure of claim 25 wherein the polymeric structure is an aircraft composite structure.

31. The polymeric structure of claim 25 wherein the polymeric structure is a boat hull.

32. A method of determining environmentally induced degradation of a polymer, the method comprising the steps of:
   adding conductive particles to the polymer to form a conductive composite comprising a preselected weight percent of conductive particles;
   making an electrical connection with the conductive composite and measuring a resistivity of the conductive composite; and
   equating the resistivity of the conductive composite with the resistivity of a previously environmentally degraded sample of the conductive composite to determine the degradation of the polymer;
   wherein a decrease in a resistivity correlates to an age degraded state of the polymer.

33. The method of claim 32 wherein said degraded state of the polymer is a decrease in specific volume with age.

34. The method of claim 32 wherein said degraded state of the polymer is an increase in density of the polymer with age.

35. The method of claim 32 wherein said degraded state of the polymer is a reduction of elongation at break with age.

36. The method of claim 32 wherein said degraded state of the polymer is a loss of volatile fractions with age.

37. The method of claim 32 wherein said equating the resistivity of the conductive composite with the resistivity of a previously-degraded sample of the conductive composite is performed at several temperatures and Arrhenius methodology is used to predict the remaining life of the polymer.

38. A method of determining environmentally induced degradation of a polymer, the method comprising the steps of:
measuring the resistivity of a composite sensor made of said polymer and a conductive filler;
equating a reduction of resistivity of said composite sensor to an environmentally degraded state of said polymer wherein said reduction of resistivity results from volumetric shrinkage of said polymer from aging.

39. The method of determining degradation of a polymer of claim 38 wherein said degraded state is a reduction of elongation of said polymer.

40. The method of determining degradation of a polymer of claim 38 wherein said degraded state is a densification of said polymer.

41. The method of determining degradation of a polymer of claim 38 wherein said degraded state is a loss of volatile components of said polymer.

42. The method of determining degradation of a polymer of claim 38 wherein said sensor is disposed in a product made of said polymer.

43. The method of determining degradation of a polymer of claim 42 wherein said sensor is disposed on a surface of a product made of said polymer.

44. The method of determining degradation of a polymer of claim 42 wherein said product is electrical insulation.

45. The method of determining degradation of a polymer of claim 42 wherein said product is a polymeric aircraft structural part.

* * * * *

UNITED STATES PATENT AND TRADEMARK OFFICE
CERTIFICATE OF CORRECTION

PATENT NO. : 7,414,416 B2
APPLICATION NO. : 10/506518
DATED : August 19, 2008
INVENTOR(S) : Watkins, Jr. et al.

It is certified that error appears in the above-identified patent and that said Letters Patent is hereby corrected as shown below:

The title page, showing an illustrative figure, should be deleted and substitute therefor the attached title page.

Formal drawings (Sheets 1-8), attached, replace informal drawings (Sheets 1-8) as issued.

Signed and Sealed this

Twenty-ninth Day of June, 2010

David J. Kappos
*Director of the United States Patent and Trademark Office*

(12) United States Patent
Watkins, Jr. et al.

(10) Patent No.: US 7,414,416 B2
(45) Date of Patent: Aug. 19, 2008

(54) ELECTRICAL CONDITION MONITORING METHOD FOR POLYMERS

(75) Inventors: Kenneth S. Watkins, Jr., Dahlonega, GA (US); Shelby J. Morris, Hampton, VA (US); Daniel D. Masakowski, Worcester, MA (US); Ching Ping Wong, Duluth, GA (US); Shijian Luo, Boise, ID (US)

(73) Assignee: Polymer Aging Concepts Inc., Dahlonega, GA (US)

( * ) Notice: Subject to any disclaimer, the term of this patent is extended or adjusted under 35 U.S.C. 154(b) by 108 days.

(21) Appl. No.: 10/506,518

(22) PCT Filed: Mar. 5, 2003

(86) PCT No.: PCT/US03/06844

§ 371 (c)(1),
(2), (4) Date: May 9, 2005

(87) PCT Pub. No.: WO03/076953

PCT Pub. Date: Sep. 18, 2003

(65) Prior Publication Data

US 2005/0268734 A1    Dec. 8, 2005

Related U.S. Application Data

(60) Provisional application No. 60/362,157, filed on Mar. 6, 2002.

(51) Int. Cl.
| | |
|---|---|
| G01N 17/00 | (2006.01) |
| G01N 33/44 | (2006.01) |
| G01N 27/04 | (2006.01) |
| G01N 27/20 | (2006.01) |
| G01R 31/12 | (2006.01) |

(52) U.S. Cl. .............. 324/693; 73/866; 324/71.1; 324/543

(58) Field of Classification Search ........ 73/865.9–866, 73/865.6, 786, 802; 324/543–544, 693, 691, 324/541, 555, 71.1
See application file for complete search history.

(56) References Cited

U.S. PATENT DOCUMENTS

| | | | |
|---|---|---|---|
| 3,603,142 A | | 9/1971 | Saylak et al. |
| 4,520,341 A | * | 5/1985 | Miyoshi et al. ............. 338/35 |
| 4,988,875 A | * | 1/1991 | Ortiz et al. ............... 250/330 |
| 5,317,252 A | * | 5/1994 | Kranbuehl ............... 324/71.1 |
| 5,432,435 A | * | 7/1995 | Strong et al. .............. 324/71.1 |
| 5,789,665 A | * | 8/1998 | Voelker et al. ............ 73/53.05 |
| 6,004,817 A | * | 12/1999 | Chamberlain et al. ........ 436/56 |
| 6,037,180 A | * | 3/2000 | Yorkgitis et al. .......... 73/866 X |

(Continued)

FOREIGN PATENT DOCUMENTS

JP         361044339 A      3/1986

(Continued)

*Primary Examiner*—Thomas P. Noland
(74) *Attorney, Agent, or Firm*—Kenneth S. Watkins

(57) ABSTRACT

An electrical condition monitoring method utilizes measurement of electrical resistivity of an age sensor made of a conductive matrix or composite disposed in a polymeric structure such as an electrical cable. The conductive matrix comprises a base polymer and conductive filler. The method includes communicating the resistivity to a measuring instrument and correlating resistivity of the conductive matrix of the polymeric structure with resistivity of an accelerated-aged conductive composite.

45 Claims, 8 Drawing Sheets

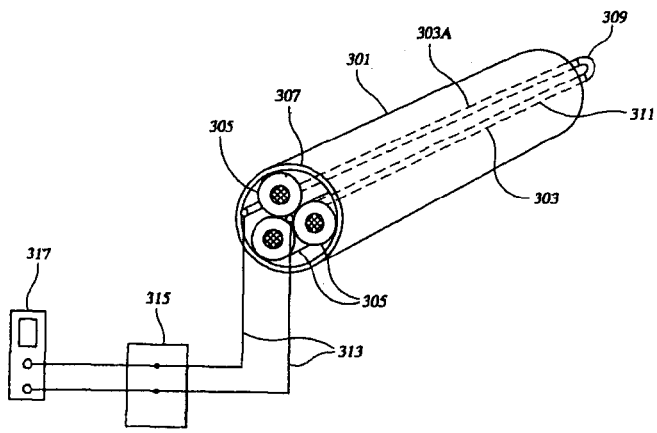

Elongation at break versus aging time for sample with 25% carbon black

Volume Change versus Aging time

*Density of sample with 25% carbon black versus aging time at 125C*

*Restivitivity versus aging time for sample with 25% carbon black loading (aging temperature: 125C, measured one day after the sample was taken out)*